(12) United States Patent
Henderson et al.

(10) Patent No.: US 11,823,789 B2
(45) Date of Patent: Nov. 21, 2023

(54) COMMUNICATION SYSTEM AND METHOD FOR MEDICAL COORDINATION

(71) Applicants: Timothy Henderson, Weehawken, NJ (US); Quenten Cothren, Canton, GA (US)

(72) Inventors: Timothy Henderson, Weehawken, NJ (US); Quenten Cothren, Canton, GA (US)

(*) Notice: Subject to any disclaimer, the term of this patent is extended or adjusted under 35 U.S.C. 154(b) by 1077 days.

(21) Appl. No.: 15/041,872

(22) Filed: Feb. 11, 2016

(65) Prior Publication Data
US 2017/0235897 A1 Aug. 17, 2017

(51) Int. Cl.
| | | |
|---|---|---|
| G16H 40/20 | (2018.01) | |
| G16H 40/40 | (2018.01) | |
| G16H 15/00 | (2018.01) | |
| G16H 40/67 | (2018.01) | |
| G06Q 10/10 | (2023.01) | |

(52) U.S. Cl.
CPC .......... *G16H 40/20* (2018.01); *G06Q 10/10* (2013.01); *G16H 15/00* (2018.01); *G16H 40/40* (2018.01); *G16H 40/67* (2018.01)

(58) Field of Classification Search
CPC ... G06F 19/328; G06F 19/3418; G16H 40/40; G16H 15/00; G16H 40/20; G16H 40/67; G06Q 10/10
See application file for complete search history.

(56) References Cited

U.S. PATENT DOCUMENTS

| | | | |
|---|---|---|---|
| 5,842,173 A | 11/1998 | Strum | |
| 6,223,137 B1 | 4/2001 | McCay | |
| 7,518,502 B2 | 4/2009 | Austin | |
| 7,590,550 B2 * | 9/2009 | Schoenberg | ..... G06Q 10/06375 |
| | | | 705/2 |
| 7,885,441 B2 | 2/2011 | Node-Langlois | |
| 8,140,160 B2 | 3/2012 | Pless | |
| 8,600,681 B2 | 12/2013 | Hayter | |
| 8,812,125 B2 | 8/2014 | Kaula | |
| 2004/0122711 A1 | 6/2004 | Miller | |
| 2005/0015508 A1* | 1/2005 | Hankejh | ................ G06Q 10/10 |
| | | | 709/230 |
| 2005/0052527 A1* | 3/2005 | Remy | .................... H04N 7/181 |
| | | | 348/14.08 |
| 2006/0165310 A1 | 7/2006 | Mack | |

(Continued)

*Primary Examiner* — Gregory D. Moseley
(74) *Attorney, Agent, or Firm* — Christopher Mayle; Bold IP, PLLC

(57) ABSTRACT

The invention includes remote-participation of a medical device manufacturing company representative in a medical procedure, whereby the device representative uses a variety of components to track and monitor devices in an operating room in "real-time," while checking on device status and advising a surgeon through Wearable Video Technology rather than being physically present in the operating room. A system allows for a remote surgeon to advise surgeons, prepares for surgeries, chooses and tracks implant devices, evaluates and reports on device implantation, calibration and performance, evaluates surgeries and staff, prepares for and concludes procedures, trains medical staff members, performs billing functions, performs legal compliance functions, performs inventory restocking functions, and various other functions.

1 Claim, 4 Drawing Sheets

(56) References Cited

U.S. PATENT DOCUMENTS

| | | | |
|---|---|---|---|
| 2007/0231190 A1 | 10/2007 | Hyde | |
| 2010/0125537 A1* | 5/2010 | Baeke | G06Q 40/08 705/500 |
| 2011/0307284 A1 | 12/2011 | Thompson | |
| 2014/0200910 A1* | 7/2014 | Schoenberg | H04L 65/403 705/2 |
| 2014/0222462 A1* | 8/2014 | Shakil | G06Q 50/22 705/3 |
| 2014/0288952 A1* | 9/2014 | Smith | G06Q 10/087 705/2 |
| 2015/0033128 A1* | 1/2015 | Curd | G16H 40/40 715/728 |
| 2015/0081327 A1* | 3/2015 | Mooker | G06Q 10/1095 705/2 |
| 2015/0149330 A1* | 5/2015 | Sweeney | G06Q 10/087 705/28 |
| 2015/0371350 A1* | 12/2015 | Zebarjadi | G06Q 10/10 705/2 |

\* cited by examiner

COMMUNICATION SYSTEM AND METHOD FOR MEDICAL COORDINATION

CROSS-REFERENCE TO RELATED APPLICATIONS

This application claims priority to U.S. Provisional Application No. 62/115,961 filed Feb. 13, 2015. The content of the above application is incorporated by reference in its entirety.

FIELD OF THE DISCLOSURE

This disclosure relates generally to the fields of electronic communication and data systems for health care management, biomedical applications for radio frequency and web based communication systems, and electronic control systems for health care professionals.

The present disclosure generally relates to communication systems and more particularly to systems, methods, and computer program products for providing an operating room communication network, thereby enabling remote interaction between individuals within and outside of the operating room.

BACKGROUND

It is not uncommon for medical procedures, such as surgeries, to involve the use of one or more medical/pharmaceutical devices that may be implanted within a patient. In fact, one forecasting model indicates that the overall demand for implantable medical devices increases 7.7% annually. That same forecasting model predicted that the market for implantable medical devices will be valued at $52 billion in 2015. Implantable orthopedic devices are the largest portion of that market, generating over $35 billion in 2014, with a projected $41.2 billion by 2019. The demand for orthopedic device implantation and utilization is likely to remain high during the next decade as the population of people over age 60 increases significantly, being that people within that age bracket tend to be more likely to require hip, knee, shoulder, and/or ankle replacements, spinal implantation procedures, open reduction procedures, internal fixation procedures for fragility fractures, and the like. Currently, approximately 90% of the demand for implantable medical devices is being met by fewer than ten medical device manufacturers.

During surgeries in which a patient receives a medical/pharmaceutical device implant, such as an orthopedic device implant, it is often the case that at least one representative of the device manufacturer will be in the operating room for at least a portion of the procedure. By being in the operating room, the representative can observe the manufacturer's device in use, calibrate the device for its intended purpose, answer questions about the device, provide instructions for how to use/configure the device, recommend additional features and/or uses of the device. Likewise, the representative has the opportunity to sell any additional devices that may be produced by the manufacturer. Sometimes, the representative's insight is so important that an operation often cannot proceed without it, such as when the representative needs to There are however, inherent problems that arise when a manufacturer representative is in the operating room during a surgery. For example, simply by being another body in the room, the representative's presence poses a risk for a variety of unwanted occurrences, such as infecting the patient, distracting surgeons and/or other members of the operating staff, getting in the way, and the like. Additionally, by utilizing the services provided by in-person representatives, a situation could arise where an operation must be delayed because the representative is not currently present. Surgical representatives are likely to be late because they are often demanded by multiple hospitals and are prone to being occupied at a different hospital/procedure, getting stuck in traffic, or by being otherwise indisposed. Such delays are the source of significant frustration in that they waste time, money, and resources, especially since operating rooms are booked in advance for blocks of time. Furthermore, because representatives are usually independent contractors or require a salary, they become an added expense that must be paid by the manufacturers they represent, and that cost gets passed along to the hospital and eventually to the patient through increased cost for the device(s).

Surgeries are further complicated in that they require several steps to be performed by several different individuals in order to be properly planned, scheduled, and executed. There are many opportunities for communication failures and, when a communication failure results, the consequences can be costly-leading to lost time and money.

There is a lack of a common system to solve the aforementioned problems. There is currently no electronic means by which these parties can communicate before, during and after surgery. Frustrations occur during surgery due to this lack of communication, and the time and money lost could be ameliorated with a centralized communication, monitoring, inventory, and interactive data system.

SUMMARY

The disclosure presented herein relates to a communication system to improve operating room coordination with surgeons, hospital staff and implant device representatives. The Virtual Rep system provides communication techniques, methods, and computer program products which facilitate the ability of surgeons, hospitals, medical staff members, and patients to receive the useful information and assistance that is usually provided by a medical device manufacturer representative, without having the representative be physically present during a surgery. Configurations that prevent unwanted information from being received, such as sales information, are also desired, as are communication systems that streamline the surgical process. In some embodiments, providing systems, methods, and computer program products which facilitate the provision of information related to one or more medical implant devices to surgeons and medical staff members without the information being given from a medical device manufacturer representative that is physically present in the operating room during a surgery. Specifically, in an embodiment, systems, methods, and computer program products are disclosed wherein audio and visual technology is used to provide a direct, real-time communication link between a single trained implant device manufacturer representative at a remote location and the staff within the operating room, including the surgeon, the operating room nurse circulator, the surgical scrub tech, and other staff members, thereby facilitating efficient and accurate planning and execution of a medical procedure, such as a surgery.

BRIEF DESCRIPTION OF THE DRAWINGS

Embodiments of the present disclosure are described in detail below with reference to the following drawings. These and other features, embodiments, and advantages of the present disclosure will become better understood with regard to the following description, appended claims, and accompanying drawings. The drawings described herein are for illustrative purposes only of selected embodiments and not all possible implementations and are not intended to limit the scope of the present disclosure. Also, the drawings included herein are considered by the applicant to be informal.

DEFINITIONS

Figure 1:
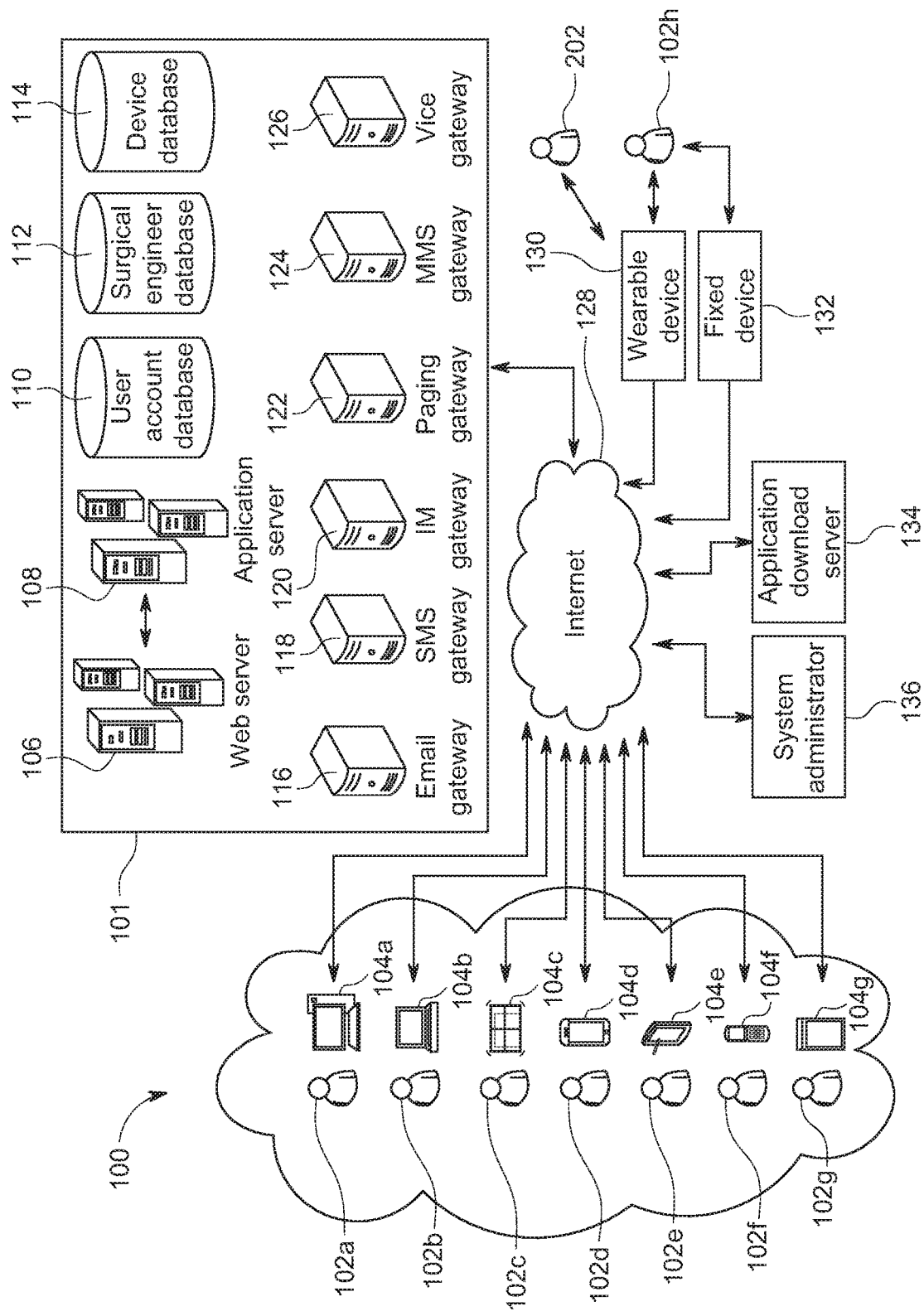
FIG. 1 is a block diagram of an embodiment of the Virtual Rep system, facilitating the coordination of a surgical procedure utilizing at least one remotely located SE surgical engineer.

Virtual Rep System: the communications system for medical workers and medical device manufacturers described herein, which aids preparation, coordination, troubleshooting, facilitation, augmentation, recording, and automatization of medical procedures.

Surgical Engineer© (hereafter "SE"): the SE is the nerve center of the Virtual Rep system: the SEC is usually a medical device representative, but here also functions as an operating room manager, a medical facility booker, an inventory clerk, a medical facility i.t. manager, and a government and/or legal system liaison. In the Virtual Rep system, the SEC© utilizes web-based technology to remotely assist the surgeon and surgical staff via wearable video and audio technology (hereinafter "WVT") such as Google Glass™, multiple cameras and monitors, a computer connected to the internet using a web application, and a server utilizing a database. The SE serves as a trained representative for a surgical/medical implant device manufacturer and therefore has substantial knowledge of the surgical/medical implant device(s) the manufacturer produces. A SE may be employed by an implant device manufacturer, or by a third party, and may be capable of participating in a medical procedure remotely.

Wearable Video Technology (hereinafter "WVT") [e.g. Google Glass™]: a very small computer that fits in a lightweight eyeglasses frame and is positioned above the eye. The glasses have a tiny video screen and camera that connect wirelessly to the internet through WiFi. The device can make and receive phone calls, send and receive texts pictures or video, or search the web. The device is controlled using one's voice and a touch pad located on one or more temple arms of the glasses frame.

Operating Room Manager: person who books surgery rooms within a hospital, coordinates staff, supplies and equipment for surgeries, supervises operating room staff and practitioners such as circulating nurses and scrub technicians, maintains compliance with internal and external governing bodies, works closely with patient safety committees and medical safety boards, coordinates the stocking and delivery of surgical implants during surgery and oversees surgical procedures as they are completed.

Billable item: non-reusable items that may be used during a medical procedure, such as gauze, stitches, bandages, and similar items, pharmaceuticals and sundries regularly priced and billed in medical procedures.

Surgical/medical implant devices: devices that may be implanted into a patient during surgery to replace existing body parts, such as knees, hips, shoulders, ankles, and the like, as well as any components and associated pharmaceuticals and supplies.

User: individuals who may utilize the system of the present disclosure, including but not limited to members of a surgical team, medical staff, SEs, and medical workers and device providers. In some embodiments, a user may be an entity, such as a hospital or a hospital department.

Medical procedure: an operation or surgery. For purposes of the Virtual Rep. system, medical procedure, surgery and operation all have the same definition: any medical process that may be performed on a patient.

Operating room: any setting in which a medical procedure may be performed on a patient, such as an actual operating room, an emergency room, a medical service provider's office, or other appropriate space.

Medical implant device manufacturer: any company that produces and/or sells surgical/medical implant devices that may be implanted into a patient in order to replace one or more body parts, such as knees, hips, ankles, shoulders, and the like, and also process facilitators like dialysis providers and pharmaceutical providers like Hep-C treatment providers. An implant device manufacturer may be, e.g., an orthopedic device manufacturer (ODM). The Representative of such a manufacturer is often a sales rep for the company.

Computer readable medium: physical and tangible entity, which may comprise "computer storage media" and "communications media."

Computer storage media: volatile and non-volatile, removable and non-removable media implemented in any method or technology for storage of information, such as computer readable instructions, data structures, program modules, or other data. Computer storage media may be, for example, and not limitation, RAM 402, ROM 404, EEPROM, Flash memory, or other memory technology, CD-ROM, digital versatile disks (DVD), or other optical storage, magnetic cassettes, magnetic tape, magnetic disk storage, or other magnetic storage devices, or any other medium which can be used to store the desired information and which can be accessed by a computer.

"Communication media": typically comprise computer readable instructions, data structures, program modules, or other data in a modulated data signal, such as carrier wave or other transport mechanism. Communication media may also comprise any information delivery media. The term "modulated data signal" means a signal that has one or more of its characteristics set or changed in such a manner as to encode information in the signal. By way of example, and not limitation, communication media comprises wired media such as a wired network or direct-wired connection, and wireless media such as acoustic, RF, infrared, and other wireless media. Combinations of any of the above are also included within the scope of computer readable medium.

Virtual Rep. Inventory Tracking System (hereinafter "VR Inventory Tracking System"): a system for tracking and evaluating medical implant devices using bar codes and/or RFID tags positioned on or near the devices, whose specs (including derivation, materials, are kept in a database accessible to secured users via the Internet and at least one server.

Virtual Rep. Interactive Audio-Visual Communication System (hereinafter "VR AV Communication System"): the system by which the SE communicates with the medical workers participating in a procedure, including cameras, web application, server, internet, database, monitor, and other computer storage media and communication media. This communication system remains connected to the VR inventory system so the SE can access inventory information before, during and after medical procedures.

DETAILED DESCRIPTION

In the Summary above and in this Detailed Description, and the claims below, and in the accompanying drawings, reference is made to particular features (including method steps) of the invention. The disclosure of the invention in this specification includes all possible combinations of such particular features.

The term "comprises" and grammatical equivalents thereof are used herein to mean that other components, ingredients, steps, among others, are optionally present. For example, an article "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The scope of "Communication System for Surgery Coordination" should be determined entirely by reference to the claims. Insofar as the description above and the accompanying drawings (if any) disclose any additional subject matter that is not within the scope of the claims below, the inventions are not dedicated to the public and Applicant hereby reserves the right to file one or more applications to claim such additional inventions.

Any element in a claim that does not explicitly state "means for" performing a specified function, or "step for" performing a specific function is not to be interpreted as a "means" or "step" clause as specified in 35. U.S.C. § 112 ¶6. In particular, the use of "step of" in the claims herein is not intended to invoke the provisions of U.S.C. § 112 ¶6.

In several embodiments, a trained implant device manufacturer representative is referred to as a "surgical engineer" © (hereafter "SE"). The SE may be professionally trained and certified within a relevant specialty/subspecialty, and known as a "Virtual Rep.-Certified© SE." Furthermore, each SE may be thoroughly knowledgeable of the various techniques, hardware, and processes of the surgeries they are associated with. In some embodiments, a SE may additionally have a personal knowledge base of each surgeon and/or staff member with whom the SE has worked. The SE may be responsible for scheduling a surgery, preparing the operating room, ordering/obtaining appropriate equipment, finding/reserving surgical assistants as necessary, educating the operating room staff, positioning the patient and the device, device calibration and the like by directly communicating with the surgeon's schedule holder, the director of the operating room, the operating room circulator, the surgeons, and other medical staff members as necessary. If necessary, the SE may additionally arrange for the provision of ancillary services by communicating with the appropriate individuals, including but not limited to cell savers, spinal cord monitors, tissue graft suppliers, surgical first assistants, and other staff member and medical industry workers. In some embodiments, the SE's job may begin immediately after a surgeon determines that a given patient is in need of a particular surgery. After surgery, the SE may track and facilitate billing and inventory supply via the VR Inventory Tracking System. The SE may also generate and monitor surgery Reports and Records through the VR AV Communication System.

In several embodiments, the VR AV Communication System functions are accomplished by a system comprising at least one stationary camera with a wide-angle lens, at least two sterile mounted operating room table cameras, at least one operating room overhead light-mounted camera, and at least one piece of Wearable Video Technology (hereinafter "WVT") for each member of the surgical team. The WVT may take the form of Google Glass™, or other similar devices. Additionally, various members of the surgical team may each utilize at least one ear-mounted, high definition, hands-free communication device.

These as well as other similar audio and visual devices may make up much of the system and may provide members within the surgical team with means to communicate information about operating room set-up, procedure organization, surgery technique, material support, and/or technical assistance as necessary, without having to engage in face-to-face interaction.

Addition to the hardware devices, the system may further comprise at least one software program or web-based application. Such a software component may allow a surgeon, SE, or any member of the surgical team or medical staff to completely plan and schedule a surgery, in concert or alone. In some embodiments, the software may be configured to recognize scannable bar codes, matrix bar codes like Quick Response™ "(QR") codes, or similar identifiers affixed to implant devices and/or billable items that may be used before, duringor after surgery. Such identifiers may help the staff locate the proper part, identify the manufacturer of the facility, staff and patient using the device, facilitate proper device positioning and calibration during a procedure, and later help with billing and restocking of the implant devices and other billable items involved in the procedure.

Embodiments of the present disclosure feature the VR AV Communication System, which facilitates real-time audio and visual communication between a surgical/medical implant device manufacturer representative and a surgical team during surgery. In some embodiments, the VR AV Communication System facilitates communication between surgical team members. In some embodiments, communication may take place before and/or after a medical procedure with various medical staff members and a medical implant device manufacturer representatives.

FIG. 1 is a block-diagram of the Virtual Rep system 100 for facilitating the coordination of a surgical procedure, utilizing at least one remotely located SE 202. Cloud-based, Internet-enabled device communication system 100 includes a plurality of users 102 accessing the VR system using computing devices 104 on a public or private network 128. The network runs on an application service provider's cloud-based, Internet-connected infrastructure 101. In some embodiments, a user application may be downloaded onto a user computing device 104 from an application download server 134 via the public or private network 128 in order to access the server-database infrastructure 101. In other embodiments, the VR server-database infrastructure 101 may be accessed via a website or web application.

Multiple users 102 may use the web application to access the VR server-database infrastructure 101 while communicating with one another via WVT 130 and/or fixed devices 132. Users 102 may simultaneously access the user-account database 110, SE database 112, and the device database 114. In some embodiments, an additional user 102h and SE 202 may communicate directly via WVT device 130 and/or fixed device 132 without the use of the network 128 or the server-database infrastructure 101. WVT device 130 may be any form of audio visual communication technology that may be worn on the body of user 102, including but not limited to high-definition ear-mounted hands-free devices, devices similar to Google Glass™ and other similar devices. Similarly, fixed devices 132 may be any non-wearable audio visual communication device, either portable or stationary, including but not limited to cameras, microphones, and combinations thereof.

Figure 2:
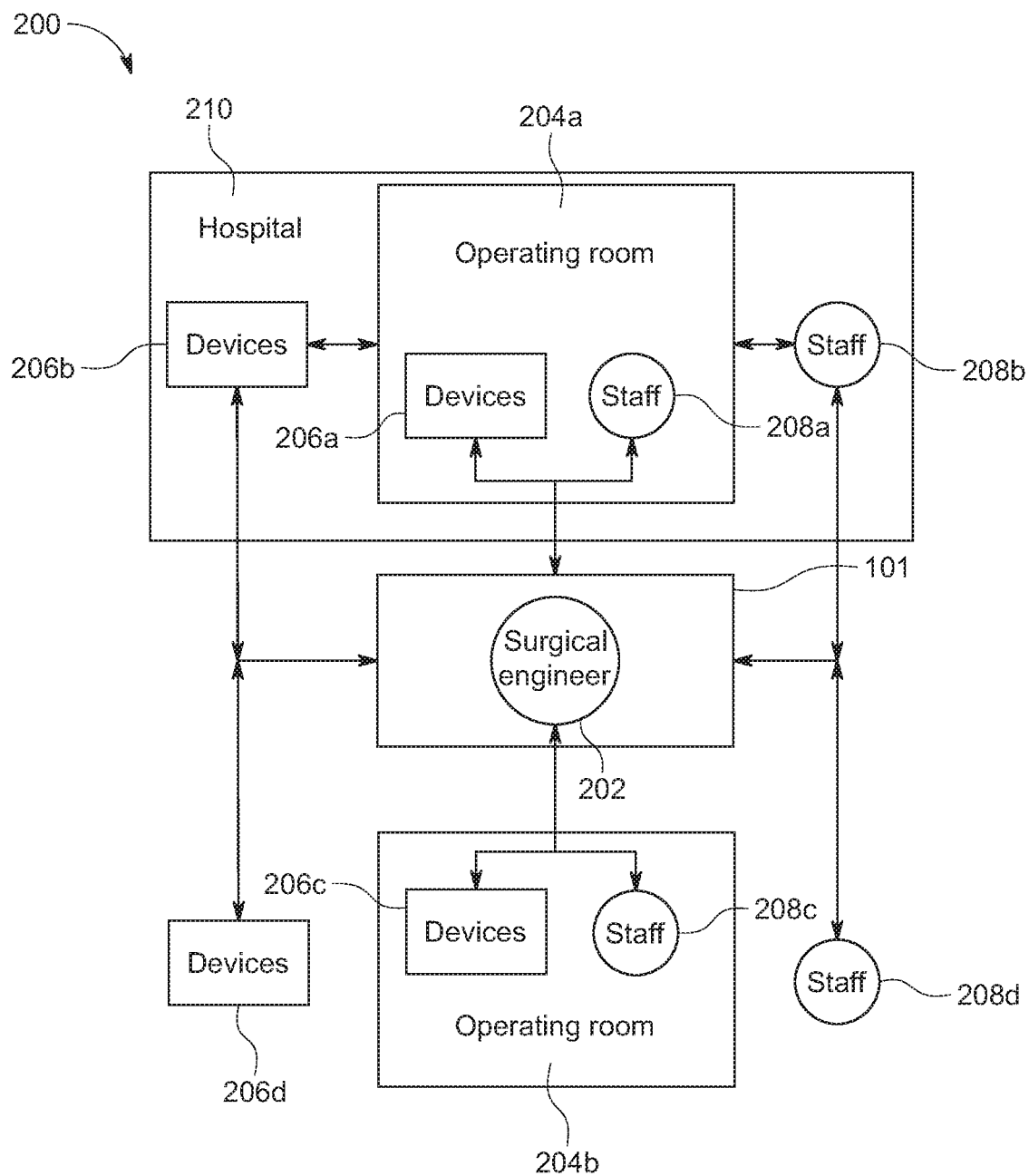
FIG. 2 is a block diagram of an embodiment of the Virtual Rep system, facilitating the coordination of a surgical procedure utilizing at least one remotely located 9B surgical engineer, according to an embodiment of the present disclosure.

FIG. 2 illustrates how the VR AV Communication System uses fixed devices 132 configured as a system that includes a stationary camera with a wide angle-lens, positioned to capture a real-time image of an operating room 204, including the location of trays, implant devices 206 and billable items before they are opened and billed. Additionally, fixed devices 132 may further include two sterile mounted table cameras within an operating room 204 allow the SE 202 to "virtually" meet with members of the surgical team, such as the surgical scrub technician, to review device 206 specs and manuals, and to prepare other surgical tools. Such review may allow the scrub technician to properly organize the surgical back table of operating room 204, as well as help the scrub technician prepare each device 206 for proper insertion. Furthermore, fixed device 132 may incorporate a camera that may be mounted to the operating room overhead light to allow SE 202 to monitor the entire procedure being performed on the patient, commenting on the operating techniques used. The overhead light camera may additionally provide SE 202 with the opportunity to troubleshoot and/or provide assistance regarding one or more devices 206 during a procedure.

In various embodiments, user computing device 104 may be configured as a desktop computer 104a; a laptop computer 104b; a tablet or mobile computer 104c; a smart phone (alternatively referred to as a mobile device) 104d; a Personal Digital Assistant (PDA) 104e; a mobile phone 104f; a hand-held scanner 104g; any commercially-available intelligent communications device. Such computing devices may comprise sensors such as a camera, a CCD, a near-field communications transceiver, a Bluetooth™ chip, infrared communication methods, wireless technology such as those using IEEE 802.15.1 or similar standards, a GPS sensor, and similar devices. Such sensors may be configured to detect the environmental elements, physical assets, and the like.

An application service provider's cloud-based, communications infrastructure (101-136) may include one or more web servers 106, one or more application servers 108, user account databases 110, SE databases 112, device databases 114, an email gateway 116, short message service (SMS) gateways 118, Instant Message (IM) gateways 120, paging gateways 122, a multimedia messaging service (MMS) gateways 124, one or more human users of the system (102a-h) and voice gateways 126. In various embodiments, one or all of the databases 110, 112 and 114 are supplied and maintained by a third-party.

User account database 110 contains account information for each user 102 of the system 100, including but not limited to login credentials, user location information, name of hospital and doctor with whom the user 102 is affiliated, scheduling calendars, types of computing devices 104 used at the facility, type of WVT devices 130 used at the facility, types of fixed devices 132 used at the facility, types of surgeries previously performed by the doctor and the facility, surgical team members with whom the user has previously worked, user account settings, user preferences, and similar data. When the user 102 is a medical facility, the user account database 110 may include information about the facility, such as type of facility, location of the facility, rooms contained within the facility, the facility's scheduling system, and similar useful data.

SE database 112 contains information regarding each manufacturer, each device, each medical staff worker, and each SE 202 who is associated with the system 100, including but not limited to specialty area, manufacturers associated with each device, scheduling calendars of staff members, types of procedures previously involving the device, quality ratings of the device, facility ratings and similar useful data.

Device database 114 contains information regarding every surgical/medical implant device 206 associated with system 100, including but not limited to the device name, a device description, composition material(s), device manufacturer information, intended use(s), installation parameters, hazardous reactions with other devices or bodily systems, inventory count of the device, device location, and other useful information about the device.

In some embodiments, medical implant devices 206 and their packaging containers are logged into the system 100 with device identifiers. Device identifiers include bar codes, RFID tags, numerical codes, color codes, Quick Response (QR)™ codes or similar identification methods. Such identification allows the SE 202 to "virtually" monitor the location, use, re-stocking, and billing of each device 206 by scanning and reading the code. Additionally, the device identifier helps ensure the correct device 206 is used in a given procedure. By way of example and not limitation, the identifier may give SE 202 the ability to verify that the correct size, type, and side (right or left) device 206 is being utilized. Identifiers are also affixed to trays, stocking shelves, surgical consumables like gauze, syringes, thread, and solvents, as well as various surgical tools, in order to facilitate quick and accurate preparation and use of these items. In some embodiments, identifiers are integrated with accounting and/or billing software that directly bills for items as they are scanned and used.

Access to the VR system may be permanently purchased or accessed as a paid "guest," accessed through free registration, through paid subscriber-registration, and/or pay-per-use basis, through a maintained, dedicated web site or web sites on the Internet 128. The VR system 100 is therefore scalable.

In one embodiment, various screens would be generated by server 106 in response to input from users 102 over Internet 128. In such an embodiment, a typical web server 106 runs a server application at a website which maintains web pages in response to Hypertext Transfer Protocol (HTTP) or Hypertext Transfer Protocol Secured (HTTPS) commands from remote browsers on various computing devices 104 used by various users 102. Thus, the server 106 is able to provide a graphical user interface (GUI) to users 102 of system 100 as web pages. The web pages are sent to the user's (and the SE and the doctor's) PC, laptop, mobile device, or PDA device 104, and are then accessed via the GUI.

Alternate embodiments of the present disclosure may include providing a tool for facilitating content sharing, coupled with a producer-designated physical asset to devices 104 as a stand-alone system (e.g., installed on one server PC) or as an enterprise system wherein all the components of infrastructure 100 are connected and communicate via a Wide Area Network (WAN) or Local Area Network (LAN). For example, in an embodiment where users 102 are all personnel/employees of the same facility, the system may be implemented as a stand-alone system, rather than as a web service (i.e., Application Service Provider (ASP) model utilized by various unassociated/unaffiliated users) as shown in FIG. 1.

FIG. 2 is a block diagram illustrating one configuration 200 of the VR system 100 for coordinating a surgical procedures using at least one remotely located SE 202, the internet-connected database system 101, and one or more pieces of WVT 102. In an embodiment, the SE 202 communicates remotely with other users 102, people in the operating room 204, implant devices 206, staff 208 *a-d*, and the hospital 210. Staff 208 may be a subset of users 102 that include members of a surgical team, general members of a hospital/medical staff, and/or any non-patient users 102 of the VR system 100. In some embodiments, a single SE 202 may be simultaneously assigned to multiple procedures being performed by multiple users 102.

The SE 202 may communicate with other users 102 who are located in a hospital 210. Likewise, SE 202 may communicate with users 102 in the operating room 204. The SE 202 may be in constant contact with staff 208 via the VR AV Communication System, and monitoring the implant devices 206 via the VR Inventory Tracking System through identifiers and software. By way of example and not limitation, SE 202 may answer questions about features of a device 206 about how to configure a device 206, help staff 208 with problems regarding device 206 implantation, instruct staff 208 on which device 206 model to use, assist staff 208 regarding the selection of surgical tools and their use, and generally monitor procedures involving one or more device(s) 206 to ensure procedures are properly performed. This smooth communication of SE 202 with staff 208, free the surgeons from distractions and clerical tasks. By communicating from a remote location, SE 202 reduces the need for medical implant device manufacturer representatives to be physically present in operating room 204 during a medical procedure. Removing extra bodies from the operating room 204 lowers the chance of patient infection and increases the efficiency of the facility.

In an embodiment, the SE 202 may perform a significant portion of the tasks related to a given medical procedure process. The SE 202 may help with prepping operating room 204; guiding the physical positioning of the patient; completing various sterilization processes; identifying and obtaining various devices and tools that may be needed; scheduling operating room 204 and staff 208; prepping and organizing billable items and implant device(s) 206; and performing similar functions. Some or all of these tasks may be performed by utilizing office-based software, which may include customizable checklists. In addition to the SE 202, other users 102 may use the software to perform similar tasks, including but not limited to obtaining insurance clearances and pre-operative clearances, arranging and managing the surgery schedule for the hospital 210, and performing similar tasks. Any user 102 may use the software to view a current surgical procedure, monitor the procedure process for accuracy, critique the procedure, send notifications regarding procedures, evaluate procedure time-lengths, predict what hospital rooms and equipment a procedure will require, and perform similar functions. In some embodiments, a surgical procedure may be reviewed at a later time by one or more users 102 in order to evaluate it, such as for liability purposes.

The SE 202 may serve as the liaison between user 102 and implant device manufacturer. Thus, a significant degree of trust and familiarity is often established between users 102 and the SEs 202. Additionally, the VR system 101 can verify if surgeons 202 have received significant training and certification in surgical techniques, as well as training regarding the use of various implant devices 206 and other surgical tools. The VR system then provides objective validation of the credentials and knowledge of SE 202. By having a single liaison between implant device manufacturers and users 102, the surgical procedure process itself may proceed more efficiently than when independent contractors revolve in/out of the operating room. Because of its reliable software and systems, the VR system ensures that a given procedure may proceed even when a particular SE 202 is unavailable. All the relevant process steps and information may be accessed by another SE 202 via computing devices 104. The SE may begin work on a surgical procedure immediately after it is determined that a particular patient needs a surgery.

In some embodiments, implant devices 206 are stored in a specific location, either within operating room 204, within hospital 210, or remotely. In such embodiments, prior to the start of a procedure, SE 202 may direct staff 208 as to which device(s) 206 will be needed, and will arrange for their retrieval and delivery. Once the appropriate devices 206 are obtained, the SE 202 may provide instructions on how to organize and prepare them for the upcoming procedure.

Figure 3:
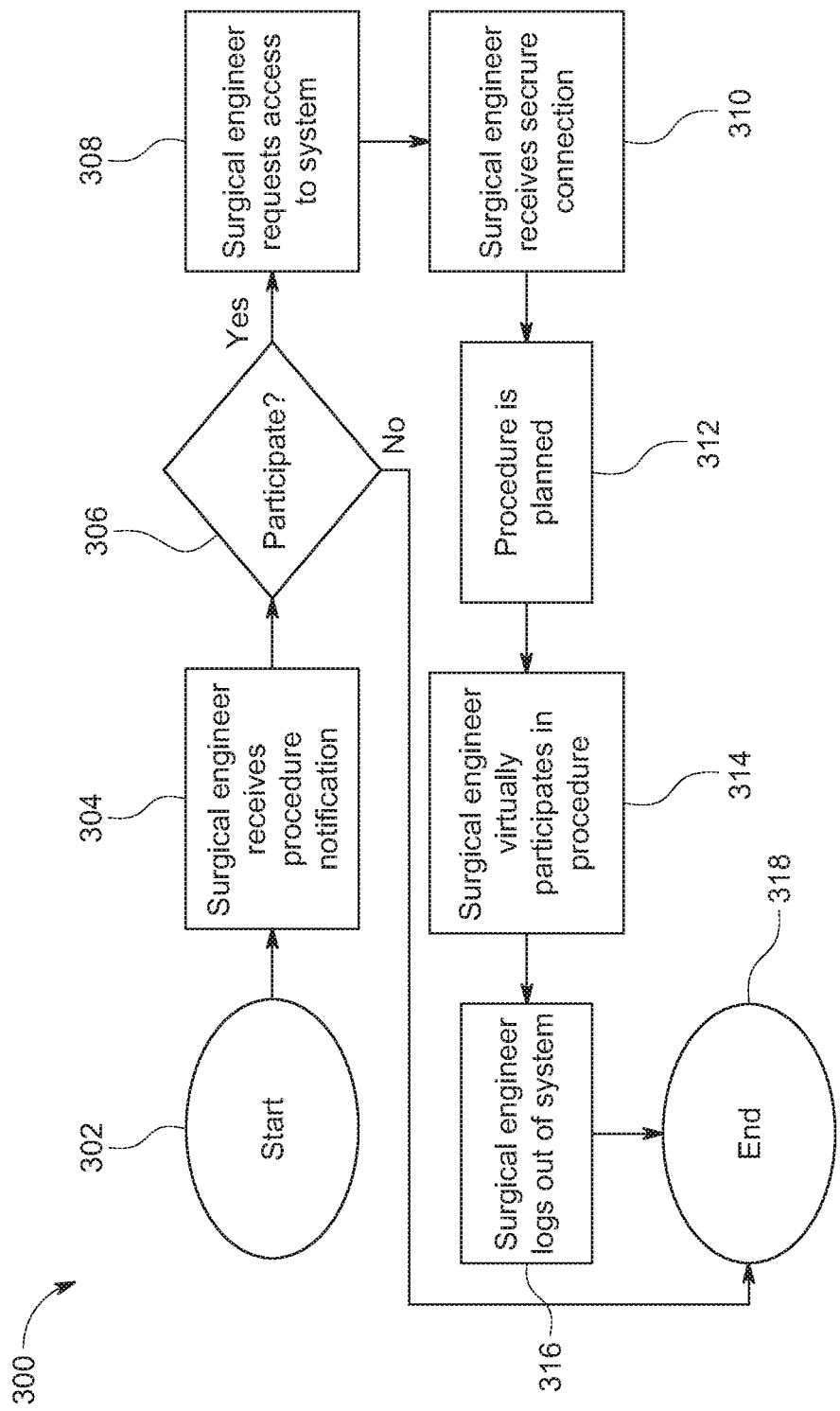
FIG. 3 is a flow chart illustrating an exemplary process for coordinating a surgical procedure utilizing at least one remotely located surgical engineer.

FIG. 3 is a flow-chart illustrating the process 300 by which a remotely-located SE coordinates a surgical procedure. The process 300 begins at step 302 when the doctor determines a procedure is needed. The SE 202 then receives a procedure notification 304. A procedure notification may come to SE 202 by way of computing device 104 in the form of an email, Instant Message, text message, or similar means. The procedure notification functions to apprise SE 202 that an operation is going to be performed that involves at least one device 206 from a manufacturer that SE 202 is affiliated with. In some embodiments, the procedure notification serves as an assignment mechanism—SE 202 is required to participate in the procedure.

In other embodiments, SE 202 has the discretion to either accept or decline participation in the procedure, whereby another SE is requested. In other embodiments, each SE 202 goes into a queuing system wherein one of a plurality of VR-certified SE's can accept the job. The process selects an SE based on parameters contained in the VR database system 110-114 (e.g. location, type of device, manufacturer, experience of SE and of surgical staff involved, type of procedure, facility technology, knowledge of surgeon, etc). In some embodiments, the notification may come from a surgeon or similar user 102 who is attempting to schedule a surgery using the VR system software.

At step 306, SE decides whether to participate in the procedure for which notification was received. If the decision is in the affirmative, process 300 proceeds to step 308 wherein SE logs into the VR system. If the decision is in the negative, process 300 proceeds to step 318, termination.

At step 308, SE 202 requests access to system 100. If SE 202 has accessed system 100 before, then there request may simply be in the form of providing valid login credentials and indicating a desire to participate in the indicated procedure. If SE 202 has not previously accessed system 100, then SE engages in a registration process in order to validate the identity of SE 202 by verifying which manufacturer SE 202 is associated with, as well as what qualifications and certifications SE 202 has.

At step 310, SE 202 establishes a secure connection to system 100 via computing device 104. Such secure connection may ensure that all of the data transmitted between computing device 104 and the rest of system 100 is protected from unauthorized entities. At step 312, SE 202 works with staff 208 to plan the procedure. Using various forms of audio and visual communication technology in the VR AV Communication System and the VR Inventory Tracking System, SE 202 may indicate which implant devices 206 will be needed, determine how those devices 206 should be configured, choose where the devices 206 will be located within operating room 204, and perform additional planning steps. Also, SE 202 may complete some or all of the general procedure preparation steps, including but not limited to scheduling operating room 204 at hospital 210, scheduling an appropriate number and type of staff 208 to be present during the procedure, and similar scheduling tasks.

At step 314, SE 202 "virtually" participates in the procedure remotely via audio visual communication technology of the VR AV Communication System. SE 202 observes the procedure to make sure it is done properly with regard to any devices 206. Additionally, SE 202 is available to provide real-time feedback on which devices 206 to use, how to use them, how to configure them, what features they have, and similar data. The SE 202 may further provide real-time trouble-shooting answers to questions that arise regarding device(s) 206. In some embodiments, SE 202 may recommend additional features or add-on components for a given device 206 that may be helpful given particular combinations of devices 206b, hospitals 210 and staff 208a.

Real-time trouble-shooting is accomplished by the SE verifying device and manufacturer specs via the VR databases 110, 112 and 114 and Servers 106 and 108, and then communicating with medical staff 208d via WVT devices 130. The SE can also give advice on device 206 calibration, patient reactions, and can advise the surgeon on implant technique and calibration via WVT 130 devices and constantly checking the VR Inventory Tracking System. The SE also facilitates communication and feedback to various parties, plans better future procedures, and reports on previous procedures using communication media 102a-g, databases 110, 112, 114, servers 120, 122, 126 and WVT devices 130.

At step 316, the conclusion of the procedure, SE 202 logs out of system 100 in order to close the secure connection, thus maintaining the confidential nature of the VR System and protecting the confidentiality of patient and staff. In some embodiments, SE generates reports of the procedure, providing information that includes procedure ratings, which device(s) 206 were used, how device(s) 206 were configured, which members of staff 208 participated, and other relevant inputs.

SE also facilitates the production of a report on the surgery and the device's implementation. SE inputs the status of implant devices and helps with restocking, as well as evaluates hospital staff and reports to any necessary insurance and legal bodies.

Process 300 is terminated by step 318 and process 300 ends. Upon completion of a procedure, a SE can log off the VR system, and then immediately begin a new procedure 306 at a different hospital 210 using entirely different devices 206.

Figure 4:
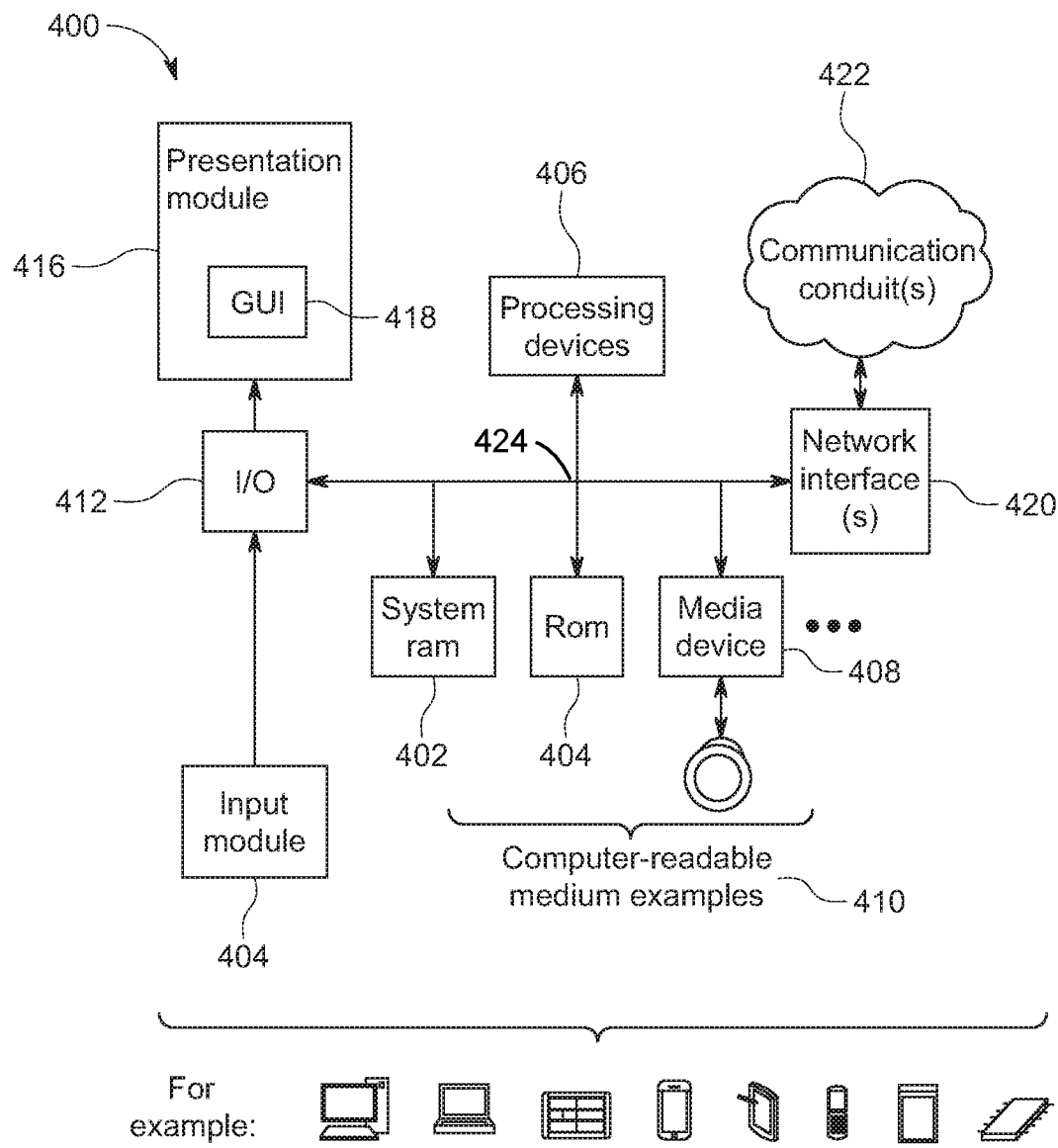
FIG. 4 is a block diagram of a computing system useful for implementing embodiments of the present disclosure.

FIG. 4 illustrates computer functionality 400 that may be used to implement the VR system. The system includes a web server 106, application server 108, user account database 110, SE database 112, device database 114, one or more gateways 116, 118, 120, 122, 124, 126, computing devices 104 utilized by users 102 to access Internet 128, or any other component of system 100. In all cases, computing functionality 400 represents one or more physical and tangible processing mechanisms.

Communications 422 may occur over a local area network or a wide area network over the Internet 128. Communication conduit(s) 422 may include any combination of hardwired links, wireless links, routers, or gateway functionality 420 servers 134, governed by one or more of a variety of protocols.

What is claimed is:

1. A system for coordinating a medical procedure comprising:
   a communication system for receiving and sending audio and video signals and data, wherein said communication system comprises one or more cameras and one or more microphones;
   a medical facility wherein said medical facility is configured to house a performance of the medical procedure performed by one or more medical personnel; and
   a virtual medical device notification system, wherein said virtual medical device notification system is configured to remotely facilitate participation of a surgical engineer in said medical procedure by performing steps of:
   automatically transmitting a request from the communication system for the surgical engineer to participate in the medical procedure;
   receiving confirmation of the participation of the surgical engineer;
   receiving confirmation of secure connection with the surgical engineer;
   using the communication system to indicate at least one medical device will be needed in the one or more medical procedure;
   verifying at least one medical device installation and calibration requirements are met;
   using the communication system to advice the medical personnel of proper medical device installation and calibration techniques;

using the communication system to provide audio and video communication between the medical personnel and the surgical engineer during the one or more medical procedure;

storing information regarding the at least one medical device including composition material, installation parameters, and hazardous reactions with other devices and bodily systems, inventory count of the at least one medical device, and at least one medical device location;

transmitting medical device installation and performance data to the surgical engineer upon conclusion of the procedure;

placing a plurality of surgical engineers in a virtual queue;

selecting the surgical engineers in the virtual queue;

presenting the surgical engineer with an option to accept or decline participation in the procedure, whereby another surgical engineer is requested if participation is declined;

determining, after an affirmative decision by a selected surgical engineer, if the selected surgical engineer has accessed the system previously, wherein if the selected surgical engineer has not accessed the system previously, engaging in a registration process to validate an identity of the surgical engineer, wherein if the selected surgical engineer has accessed the system previously, requesting login credentials of the selected surgical engineer;

providing the surgical engineer a customizable checklist for the medical procedure;

providing the surgical engineer a process obtaining insurance clearances and pre-operative clearances;

arranging and managing a surgery schedule for a hospital in a first user interface;

presenting users of the system the medical procedure to monitor the procedure process for accuracy and critique the procedure wherein the system permits the users to evaluate time-lengths of the medical procedure; and transmitting notifications regarding the surgical procedure and evaluate the time-lengths.

\* \* \* \* \*